(12) United States Patent
Polkus

(10) Patent No.: US 6,447,164 B1
(45) Date of Patent: Sep. 10, 2002

(54) X-RAY IMAGING SYSTEM WITH VIEWABLE BEAM ANGULATION ADJUSTMENT

(75) Inventor: Vincent S. Polkus, Delafield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 62 days.

(21) Appl. No.: 09/656,790

(22) Filed: Sep. 7, 2000

(51) Int. Cl.7 ................................................ A61B 6/08
(52) U.S. Cl. ...................................... 378/206; 378/205
(58) Field of Search ................................. 378/206, 205, 378/19

(56) References Cited

U.S. PATENT DOCUMENTS 5,388,143 A * 2/1995 MacMahon ................. 378/206
5,572,568 A * 11/1996 Kanemitsu .................. 378/206
6,056,437 A * 5/2000 Toth ........................... 378/205
6,106,152 A * 8/2000 Thunberg .................... 378/205

* cited by examiner

Primary Examiner—Robert H. Kim
Assistant Examiner—Irakli Kiknadze
(74) Attorney, Agent, or Firm—Peter J. Vogel, Esq.

(57) ABSTRACT

In an X-ray imaging system having a detector and a tube disposed to project an X-ray beam field into the plane of the detector, visual indicators associated with the detector and the X-ray beam field, respectively, are provided for use in aligning the detector and beam field. A computational device is also provided for producing a signal representing offset, caused by X-ray beam angulation, between the geometric center of the beam field and the point at which the central axis of the projected X-ray beam intersects the detector plane. A display device, responsive to the produced signal, enables a system user to compensate for the offset when aligning the detector and beam field.

20 Claims, 8 Drawing Sheets

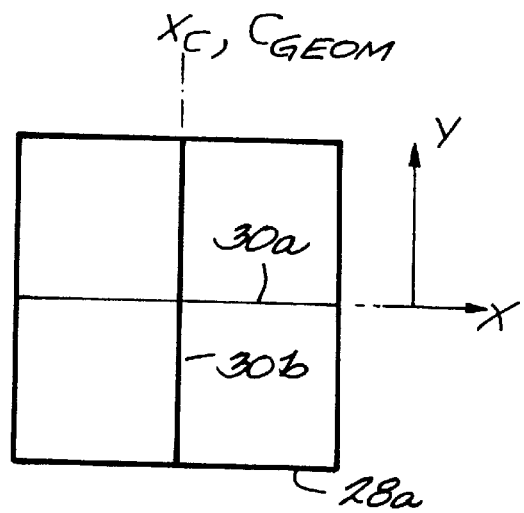
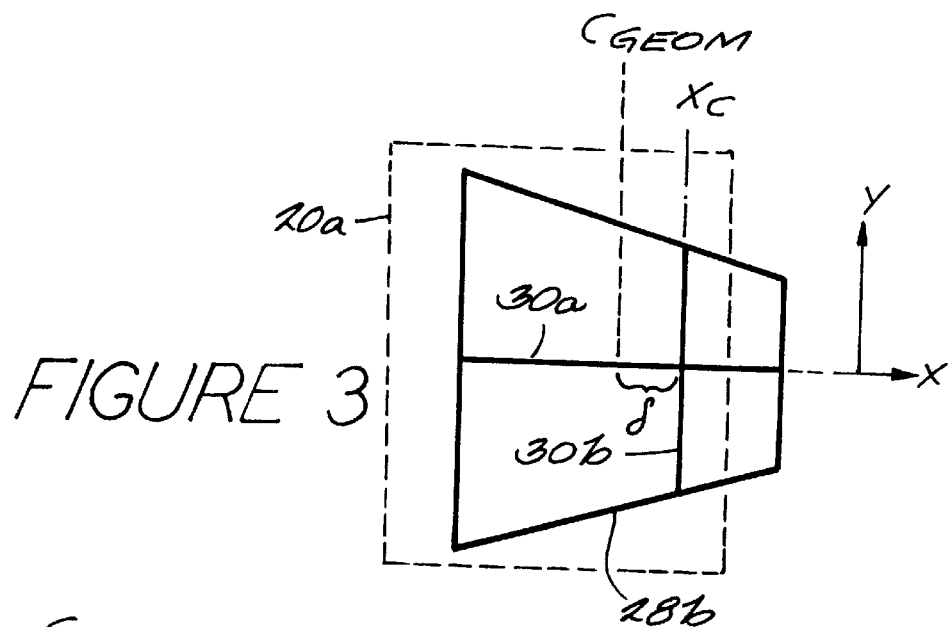
FIGURE 3
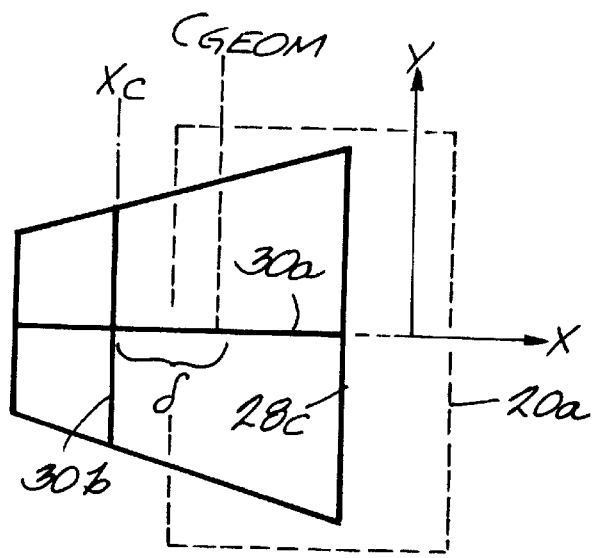

X-RAY IMAGING SYSTEM WITH VIEWABLE BEAM ANGULATION ADJUSTMENT

BACKGROUND OF THE INVENTION

The invention disclosed and claimed herein generally pertains to an X-ray imaging system for enabling a system operator to quickly align an X-ray detector with the field of a beam projected by the system X-ray tube. More particularly, the invention pertains to a system of the above type which is provided with visual elements or indicators associated with the detector and the X-ray beam field, respectively, wherein the indicators are aligned with each other to ensure proper alignment of the detector and beam field. Even more particularly, the invention pertains to a system of the above type wherein the visual indicators are automatically adjusted to compensate for distortion resulting from X-ray beam angulation.

As is well known, in a typical X-ray imaging system a patient is positioned between an X-ray tube and an image receptor having a planar imaging surface, such as an X-ray film or a digital solid state detector. The tube projects a beam of X-radiation toward the detector surface and through body structure of the patient which is to be imaged. The area of projected X-radiation which is incident on the detector defines the active imaging area (AIA). Generally, the X-ray beam field or field of view (FOV), which is defined herein to be the intersection of the projected beam and the detector plane, must be coincident with, or lie within, the boundaries of the detector surface in order to avoid loss of image data. The FOV may be adjusted by rotating or tilting the tube to vary the direction of the projected X-ray beam, and also by operating a collimator to vary the width and length dimensions of the X-ray beam. Further adjustments may be made by linear translation of the tube and/or the detector.

In an important class of X-ray imaging systems, visual indicators are provided to enable a system operator or technician to quickly align the beam field and the detector, in an effort to provide the requisite coincidence therebetween. For example, in one product of such type a patient is horizontally supported upon a table, an X-ray tube is mounted above the table to project a beam downwardly, and a film cassette or other detector is located underneath the table. To assist the operator in aligning the detector and the X-ray beam, a mark or notch is formed in the detector handle, exactly at the mid-point of the planar detector surface along its length. Also, a beam of visible or laser light is projected downward from the tube, to provide a visible light field proximate to the detector plane. The light beam is optically guided or directed so that the boundaries of the light field substantially coincide with the boundaries of the X-ray beam field which will be projected by the tube for a particular tube orientation and collimator adjustment. Axes of the light field are identified by two thin lines of shadow, which are orthogonal to each other and intersect at a point defined by the intersection of the detector plane and the central axis of the projected beam. The shadow line axes also bisect the light field, along the mid-points of its length and width, respectively. Thus, even though the operator cannot easily view the detector, since it is positioned beneath the table, the operator can readily translate the detector to align the notch in the handle with the shadow line axis nominally located at the mid-point of the light beam field length.

If the tube is oriented so that the X-ray beam, or more particularly the central axis thereof, is directed in perpendicular or orthogonal relationship to the detector plane, the beam field projected into the detector plane will be of rectangular configuration. In this circumstance, the geometric center of the projected beam field will coincide with the point at which the central axis of the beam intersects the detector plane. Accordingly, the aforesaid shadow line axis will in fact be located at the mid-point of the beam field length. In this case, aligning the shadow line axis with the notch in the detector handle will effectively center the X-ray beam field along its length with the detector surface along its length, to provide the necessary coincidence therebetween.

However, an X-ray technician or operator, when setting up for an imaging procedure, may need to angulate the beam, that is, rotate or pivot the X-ray tube so that the beam is directed toward the detector at an angle of less than 90 degrees. This may be necessary, for example, to ensure that the beam passes through the specific body structure of the patient which is to be imaged. As the X-ray beam is increasingly angulated, the beam field projected into the detector becomes correspondingly distorted and trapezoidal, and the location of the point of intersection of the central beam axis becomes offset with respect to the geometric center of the projected X-ray field. As a consequence of these decentering and distorting effects, the conventional visual indicator arrangement described above will no longer align the center of the detector with the geometric center of the beam field, but rather with a point offset therefrom. This may cause anatomical cutoff to occur during the imaging process, whereby some of the image data acquired by the X-ray beam would not be received upon the detector. This, in turn, would necessitate that the examination be repeated, thus contributing to increased procedure cycle time, higher examination costs, and higher net radiation doses to the patient.

SUMMARY OF THE INVENTION

In an imaging system provided with a detector having a plane and also with an X-ray tube spaced apart from the plane, wherein the tube projects an X-ray beam into the plane to define a beam field therein, apparatus is provided for use by a system operator to selectively align the detector and the beam field. The apparatus comprises a first viewable element which indicates the position of the detector along a reference axis lying in the detector plane, and further comprises a computational device for producing a signal representing an offset along the reference axis, between the geometric center of the beam field and the point at which the central axis of the projected X-ray beam intersects the detector plane. Structure is provided to respectively support the tube and the detector to enable relative translational movement therebetween along the reference axis. An indicator device, responsive to the produced signal, provides notice that the first element is positioned in a pre-specified relationship with the beam field geometric center.

In a preferred embodiment of the invention, the detector is provided with an X-ray detection surface lying in the detector plane, the surface having a length dimension which extends along the reference axis, and the first element comprises a visually observable element positioned at the center of the length dimension of the detector. The indicator device provides visual or viewable notice when the first element and the beam field geometric center are in alignment along the reference axis. Preferably also, the computational device is disposed to compute the offset as a function of the spacing between the tube and the detector plane, and of the angles respectively characterizing the direction and width of the projected beam.

In a useful embodiment, the indicator device comprises a linear array of light emitting diodes (LED's), or of other light emitting elements as defined hereinafter, which extends along the reference axis in parallel relationship therewith. A given one of the light elements is illuminated by the produced signal representing offset, and is available for use by an operator to align the first viewable element, and therefore the center of the detector, with the geometric center of the beam field.

In another useful embodiment, the apparatus is further provided with a second element indicating the position of the beam field axis intersection point, and with a tracking device disposed to monitor the linear travel of the detector, along the reference axis, from an initial position at which the first and second elements are in alignment.

BRIEF DESCRIPTION OF THE DRAWINGS

FIG. 3 is a schematic representation illustrating distortion of the X-ray and light beam fields which results from X-ray beam angulation.

DETAILED DESCRIPTION OF THE PREFERRED EMBODIMENT

Figure 1:
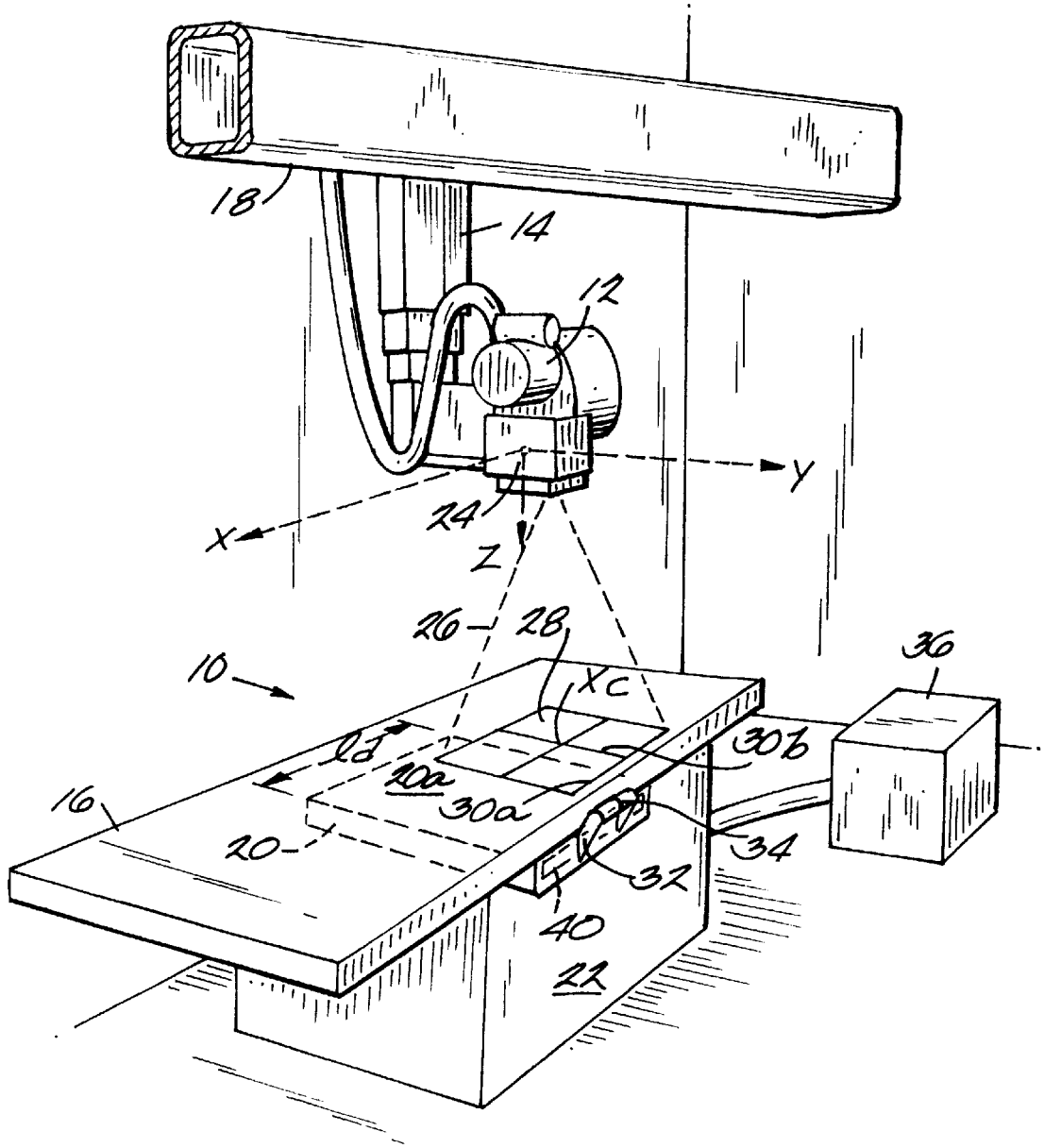
FIG. 1 is a perspective view showing components of an X-ray imaging system for use in connection with an embodiment of the invention.

Referring to FIG. 1, there is shown an X-ray imaging system 10 provided with an X-ray tube 12 which is journalled or pivotably mounted on a vertically oriented column 14. System 10 further includes a table 16 which is disposed to support a patient or other imaging subject (not shown in FIG. 1) in a horizontal plane. Usefully, column 14 is suspended from a track 18, and the tube and column may be translated along the track and along the length dimension of table 16. FIG. 1 further shows table 16 carried upon a table base 22, which also supports a flat X-ray detector 20 directly beneath the table 16. Detector 20 has a planar image receiving surface 20a of length $l_d$, and usefully comprises X-ray film or a digital solid state detector.

It is to be understood that horizontal support of a patient is shown in FIG. 1 for purposes of illustration, and is by no means intended to limit the scope of the invention. In other embodiments the patient could be placed in a vertical or other orientation, provided that the X-ray tube and detector were respectively located so that the patient was positioned between them.

After an imaging subject has been placed on table 16, X-ray tube 12 is adjusted to project a beam of X-radiation through a region of the subject to image specified body structure. The tube position may be adjusted by pivoting the tube relative to column 14, and also by translating the column and tube along the table. The dimensions of the projected X-ray beam may be adjusted by means of a collimator 24, of conventional design, which is joined to tube 12 and is traversed by the projected beam. Detector 20 is likewise mounted for translational movement along the table 16, and is disposed to receive the image of the specified body structure. However, as stated above, the detector must be properly aligned with the projected beam field or FOV, in order to ensure detection of all desired image data. FIG. 1 further shows mutually orthogonal X-, Y-, and Z-coordinate axes for reference purposes, the Z-axis being vertically oriented, the X-axis being parallel to the longitudinal dimension of table 16, and the Y-axis being transverse thereto. The center of the coordinate system is coincident with the focal spot of X-ray tube 12, and the tube is mounted for rotation about the center of the coordinate system.

To assist an operator in aligning detector 20 and the projected beam field, a configuration of optical elements (not shown) is supported proximate to tube 12 and coillimator 24. When activated by the operator, by means of a switch or the like (not shown), the optical elements project a light beam 26 downwardly, to provide a visible light field 28 on the upper surface of table 16. The optical elements are designed in connection with X-ray tube 12 and collimator 24 so that, for given tube and collimator settings, the boundaries of light field 28 will coincide with the boundaries of the FOV of a projected X-ray beam, on the upper surface of table 16. Such surface is parallel to and closely spaced from planar detector surface 20a, defining the detector plane. Thus, the boundaries of light field 28 will closely or substantially coincide with the boundaries of an X-ray beam field projected by tube 12 into the detector plane. The detector plane and the surface of table 16 are both parallel to the X-Y plane, as viewed in FIG. 1.

Referring further to FIG. 1, there are shown thin shadow line axes 30a and 30b projected upon light field 28, axes 30a and 30b being parallel to the X and Y axes, respectively. Axis 30b is centered at the midpoint of the length dimension of light field 28, and axis 30a is centered at the midpoint of the width dimension thereof. Thus, the intersection of axes 30a and 30b identifies the location of the point $X_c$ at which the central axis of light beam 26 intersects the surface of table 16. Moreover, a handle 32 is attached to detector 20, which is positioned close to the edge of the upper surface of table 16 and is provided with a very distinctive mark, notch or groove 34. The mark 34 is positioned at the mid-point of detector surface 20a, along its length dimension $l_d$. Accordingly, an operator can simultaneously view mark 34 and axis 30b of light field 28, and can readily translate detector 20 along the X-axis to align the mark 34 with the axis 30b.

Referring further to FIG. 1, there is shown an electronic device 36 for performing computations in accordance with an embodiment of the invention, as described hereinafter, and for controlling operation of a visual display device 40 positioned along the edge of detector 20. Display device 40, generically depicted in FIG. 1, can be embodied in a number of different forms or configurations. In other embodiments, a display device is positioned along the edge of table 16 rather than the detector 20. Some of these embodiments are shown hereinafter.

Figure 8:
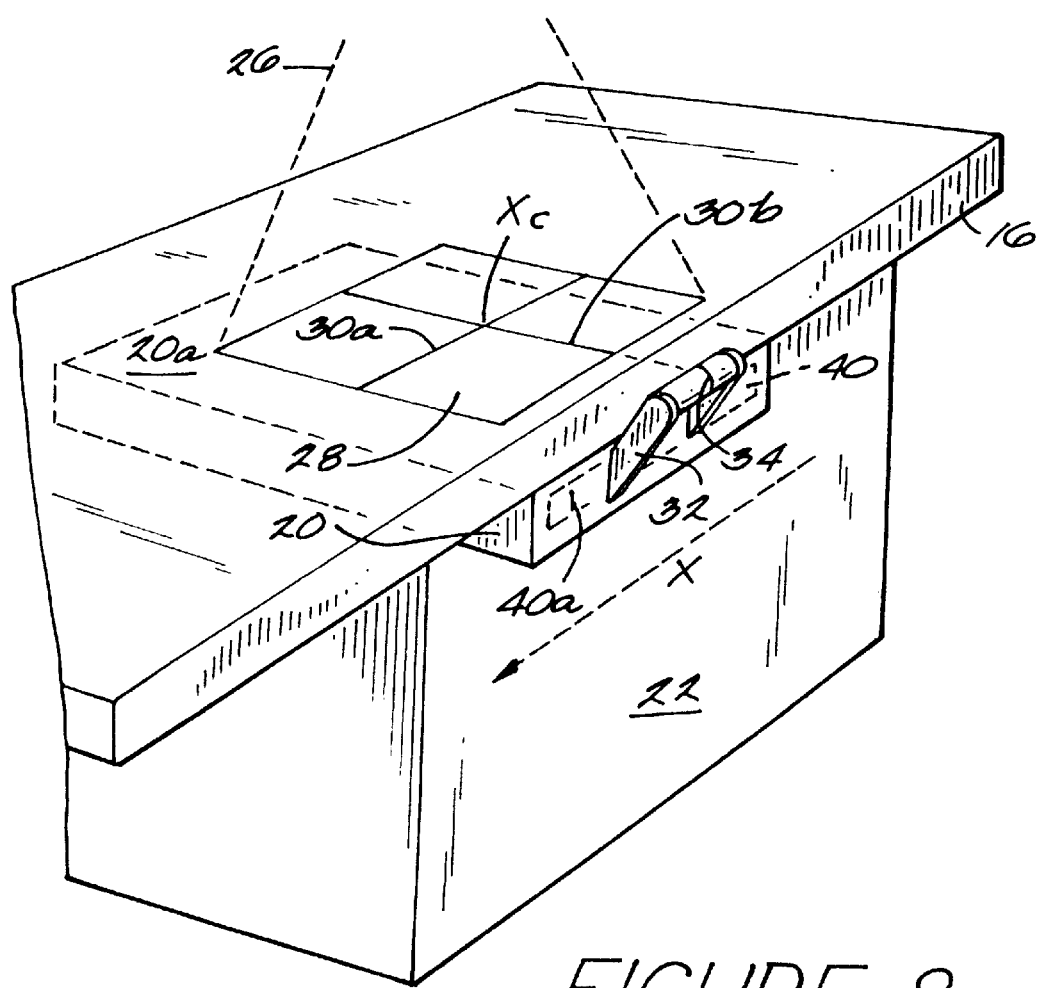
FIG. 8 is a perspective view showing a portion of the system of FIG. 1 in greater detail.

As described hereinafter in further detail, an operator of system 10 may readily use mark 34, axis 30b, and display 40 together, in order to properly align detector 20 and a projected X-ray beam field for a specified image acquisition. Referring to FIG. 8, it is seen that an operator could quite easily align the mark 34 on detector handle 32 with shadow axis 30b, simply by looking downward as the detector is translated along the X-axis. When the mark 34 on detector handle 32 is aligned with axis 30b, the detector 20 will be centered at the point $X_c$. Alternatively, the detector could be translated along the X-axis to align mark 34 with a specified viewable reference mark illuminated upon diplay 40, as described hereinafter.

Figure 2:
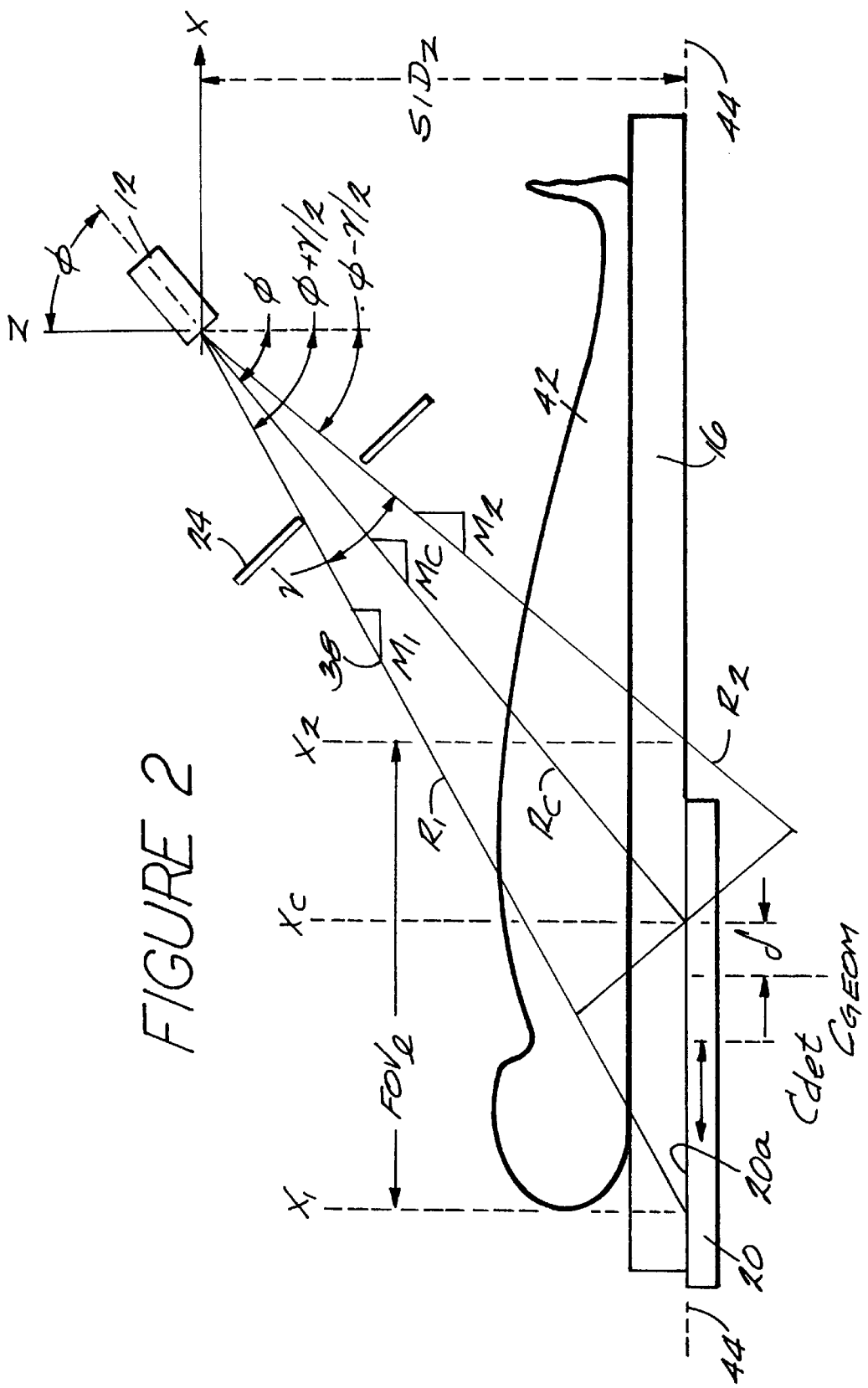
FIG. 2 is a schematic diagram showing components of the system of FIG. 1 in simplified form, together with an imaging subject, to illustrate principles of the invention.

Referring to FIG. 2, there is shown tube 12 oriented to project an X-ray beam 38 toward detector 20, through a patient 42 positioned on table 16. More specifically, tube 12 is directed so that its central ray $R_c$, comprising the beam axis, is at an angle $\phi$ with respect to the vertical Z-axis, hereinafter referred to as the beam direction angle. It is to be understood that central ray $R_c$ of beam 38 is directed toward detector surface 20a at an angle of 90° if $\phi$ is 0°, and is directed toward the detector surface at an angle of less than 90° if $\phi$ is non-zero. It is to be further understood that the principles of the invention apply to any beam direction angle $\phi$ which is less than +/−90°. Thus, beam 38 is angulated, as described above, when $\phi$ is non-zero. FIG. 2 further shows projected beam 38 to be bounded in the X-Z plane by rays $R_1$ and $R_2$ extending along its respective edges. FIG. 2 also shows beam 38 passing through collimator 24. Collimator 24 establishes the angle $\gamma$ of beam 38 in the X-Z plane, the collimator 24 being adjustable to selectively vary $\gamma$. Hereinafter, $\gamma$ is referred to as the beam width angle. Since central ray $R_c$ of beam 38 is at an angle $\phi$, it will be readily apparent that rays $R_1$ and $R_2$ are oriented to angles of $\phi+\gamma/2$ and $\phi-\gamma/2$, respectively, as shown by FIG. 2.

Referring further to FIG. 2, there is shown X-ray beam 38 intersecting detector plane 44, the plane of detector surface 20a of detector 20. This intersection defines the beam field or FOV, that is, the projection of the X-ray beam into the detector plane. As stated above, the boundaries of the light field 28 coincide, or substantially coincide, with the boundaries of the X-ray beam FOV in the detector plane. Thus, beam angulation will have substantially the same effect on the geometries of the X-ray beam FOV and the light field 28.

Referring to FIG. 3, there is shown the light field 28a which results when $\phi$ is set to 0°, so that light beam 26 is projected toward the table surface and detector plane at an angle of 90°. The beam field 28a is shown to be of symmetrical rectangular shape, and the geometric center $C_{geom}$ thereof coincides with the central beam axis intersection point $X_c$. The corresponding X-ray beam FOV, in detector plane 44, is characterized by the same geometry. Accordingly, the detector surface 20a may be aligned with the X-ray beam FOV by centering the detector surface at the point $X_c$, along the X-axis.

However, as stated above, when X-ray beam 38 and light beam 26 are angulated, by pivoting tube 12 to a non-zero angle of $\phi$ such as 45°, the beam fields respectively projected thereby become distorted. This is illustrated in FIG. 3 by the light beam field 28b, produced by an angulated light beam 26, which is shown to be of trapezoidal configuration. Moreover, FIG. 3 shows the beam axis intersection point $X_c$ of the light beam field 28b to be offset from the geometric center $C_{geom}$ thereof, along the X-axis, by an amount $\delta$. As a result, a portion of light beam field 28b is not aligned with detector surface 20a. More importantly, a portion of the FOV of the corresponding X-ray beam, projected into the detector plane, likewise is not aligned with detector surface 20a. As a result, the image data provided by such X-ray FOV portion is not received or detected.

Referring further to FIG. 3, there is shown the light field 28c produced by beam 26 when $\phi$ is set to a value such as −45°. The light field 28c is seen to be trapezoidal, in like manner with field 28b, but is distorted in the opposite direction. Also, in light field 28c the point $X_c$ is offset leftward from the geometric center along the X-axis, by an amount $\delta$, rather than rightward as shown in connection with light field 28b.

In accordance with the invention, it has been recognized that if the offset $\delta$ along the X-axis can be determined, the center mark 34 of the detector and the light field axis 30b can still be usefully employed to align the center of the detector with the geometric center of the X-ray beam FOV, notwithstanding the distorting effects of angulation described above. Loss of image data will thereby be prevented. Moreover, for a given angulation, because of the close coincidence between light field 28 and the corresponding X-ray beam field in the detector plane, the geometric centers of the two fields will be at substantially the same position along the X-axis. The central axis intersection points $X_c$ of the two fields will likewise be at substantially the same position along the X-axis. Accordingly, offset $\delta$, the spacing along the X-axis between $X_c$ and the geometric center, can be determined from a set of parameters which characterize X-ray beam 38, and the FOV projected thereby into the detector plane. Such parameters include beam direction angle $\phi$, beam width angle $\gamma$, and $SID_z$, where $SID_z$ is the source-to-image distance along the Z-axis, i.e., the distance between the tube 12 and the detector plane 44, which is a known value. The parameter set further includes the length $FOV_1$ of the X-ray beam field, i.e., its dimension along the X-axis. FIG. 2 shows this length to be the distance between $X_1$ and $X_2$, the points at which detector plane 44 is intersected by rays $R_1$ and $R_2$, respectively, of X-ray beam 38. In FIG. 2, central axis $R_c$ of X-ray beam 38 intersects detector plane 44 along the X-axis at $X_c$. $X_c$ may be readily determined from $\phi$ and $SID_z$, wherein $X_c$ equals $SID_z\tan\phi$.

While FIG. 2 shows beam 38 angulated by pivoting tube 12 with respect to the Z-axis, the beam could alternatively be angulated by pivoting or rotating detector 20. Generally, the invention is applicable for any relative movement between the tube and the detector which causes the beam direction angle $\phi$ to become less than +/−90°.

In determining the value of offset $\delta$, it is useful to first consider the slopes $M_1$, $M_2$ and $M_c$ the slopes of rays $R_1$, $R_2$ and $R_c$, respectively, as shown by FIG. 2. Each of these slopes can be defined in terms of the defined angles $\phi$ and $\gamma$, as follows:

$$M_{center} = \tan(\phi) \qquad \text{Equation (1)}$$

$$M_1 = \tan\left(\phi + \frac{\gamma}{2}\right) \qquad \text{Equation (2)}$$

$$M_2 = \tan\left(\phi - \frac{\gamma}{2}\right) \qquad \text{Equation (3)}$$

For the coordinate system described above for the X-Z plane shown in FIG. 2, the equation for a line shown therein has the generalized form $x_i = M_i z_i + b_i$, where ($x_i$, $z_i$) are coordinates of points along the line and $M_i$ is its slope. However, computational complexity can be reduced if imaging system 10 is designed so that the focal spot of tube 12 is coincident with the rotation center of the X-ray tube support device. In this case, the equations pass through the origin of the coordinate system, and the $b_i$ terms drop to 0, resulting in the expression $x_i = M_i z_i$, which is useful for describing beam rays $R_1$, $R_2$ and $R_c$. Moreover, for $z_i = SID_z$, the known source-to-image distance, respective intersection points $X_1$ and $X_2$ of rays $R_1$ and $R_2$ are given as follows:

$$X_1 = M_1 SID_z = SID_z \tan\left(\phi + \frac{\gamma}{2}\right) \qquad \text{Equation (4)}$$

$$X_2 = M_2 SID_z = SID\tan\left(\phi - \frac{\gamma}{2}\right) \qquad \text{Equation (5)}$$

It is essential to recognize that the length $FOV_1$ of the X-ray beam field can be no less than the length dimension of detector surface 20a which extends along the X-axis. Thus, $FOV_1$ is prespecified to either be equal to, or selectively less than, the length of detector surface 20a. Thus, $FOV_1$ is a known predetermined value. From FIG. 2, it is a seen that $FOV_1$ is equal to $(X_1-X_2)$. Accordingly, $FOV_1$ is related to $SID_z$, $\phi$ and $\gamma$ as follows:

$$FOV_1 = X_1 - X_2 = SID_z[\tan(\phi + \frac{\gamma}{2}) - \tan(\phi - \frac{\gamma}{2})] \quad \text{Equation (6)}$$

Using the known trigonometric relationships $$\tan(A - B) = \frac{\tan A - \tan B}{1 + \tan A \tan B} \text{ and } \tan(A + B) = \frac{\tan A + \tan B}{1 - \tan A \tan B},$$

Equation (6) can be rearranged as follows:

$$FOV_1 = \left[\frac{2(1 + \tan^2(\phi))\tan(\frac{\gamma}{2})}{1 - \tan^2(\phi)\tan^2(\frac{\gamma}{2})}\right] \times SID_z \quad \text{Equation (7)}$$

When the terms of Equation (7) are re-arranged and the equation solved, the following quadratic results:

$$A\tan^2(\frac{\gamma}{2}) + B\tan(\frac{\gamma}{2}) + C = 0 \quad \text{Equation (8)}$$

where $A=\tan^2(\phi)$, $$B = 2(1 + \tan^2(\phi)) \times \left(\frac{SID_z}{FOV_1}\right),$$

and $C=-1$. Solution of the quadratic Equation (8) gives rise to two possible solutions $$\gamma_1 = 2\tan^{-1}\left[\frac{-\left(\frac{1 + \tan^2(\phi)}{FOV_1/SID_z}\right) + \sqrt{\left(\frac{1 + \tan^2(\phi)}{FOV_1/SID_z}\right)^2 + \tan^2(\phi)}}{\tan^2(\phi)}\right] \quad \text{Equation (9)}$$

$$\gamma_2 = 2\tan^{-1}\left[\frac{-\left(\frac{1 + \tan^2(\phi)}{FOV_1/SID_z}\right) - \sqrt{\left(\frac{1 + \tan^2(\phi)}{FOV_1/SID_z}\right)^2 + \tan^2(\phi)}}{\tan^2(\phi)}\right] \quad \text{Equation (10)}$$

For the geometric state of the X-ray beam provided by imaging system 10, only the solution $\gamma_1$ provided by Equation (9) is valid. Thus, after $\gamma_1$ has been determined, collimator 24 is adjusted as required to establish the beam width angle of beam 30 at $\gamma_1$. The length $FOV_1$ is thereby set to the value prespecified therefor. Moreover, from the values of $FOV_1$, beam direction angle $\phi$, $SID_z$, and $\gamma_1$, the offset $\delta$ can be directly computed, for use in aligning the detector and the projected X-ray field. To compute $\delta$, it is noted that the geometric center $C_{geom}$ of the projected beam field 34 is defined by the average $\overline{X}$ of the coordinates $X_1$ and $X_2$, that is, $\overline{X}=(X_1+X_2)/2$. From Equations (4) and (5) for $\gamma=\gamma_1$, $\overline{X}$ may be set forth as follows:

$$\overline{X} = \frac{SID_z}{2}(\tan(\phi + \frac{\gamma_1}{2}) + \tan(\phi - \frac{\gamma_1}{2})) \quad \text{Equation (11)}$$

As stated above, $X_c$ is equal to $SID_z\tan(\phi)$. Thus, the offset $\delta$ is given by the expression:

$$\delta = \overline{X} - X_c = SID_z\left[\frac{(\tan(\phi + \frac{\gamma_1}{2}) + \tan(\phi - \frac{\gamma_1}{2}))}{2} - \tan(\phi)\right] \quad \text{Equation (12)}$$

Electronic control device 36, shown in FIG. 1 and comprising a computer control or the like, is disposed to receive the specified values of $\phi$, $SID_z$ and $FOV_1$ as inputs, and is configured to perform computations in accordance with the equations set forth above. Thus, upon receiving the specified inputs, device 36 is operated to implement Equations (7)–(9) to determine the beam width angle $\gamma_1$ corresponding to the inputs. If collimator 24 is automatically adjustable, in response to a signal, control device 36 may be further configured to couple a signal representing $\gamma_1$ to adjust collimator 24, and thereby provide autocollimation. After determining $\gamma_1$, control device 36 is operated in accordance with Equations (11) and (12) to compute offset $\delta$. Control device 36 then couples a signal representing offset $\delta$ to display device 40.

Figure 4:
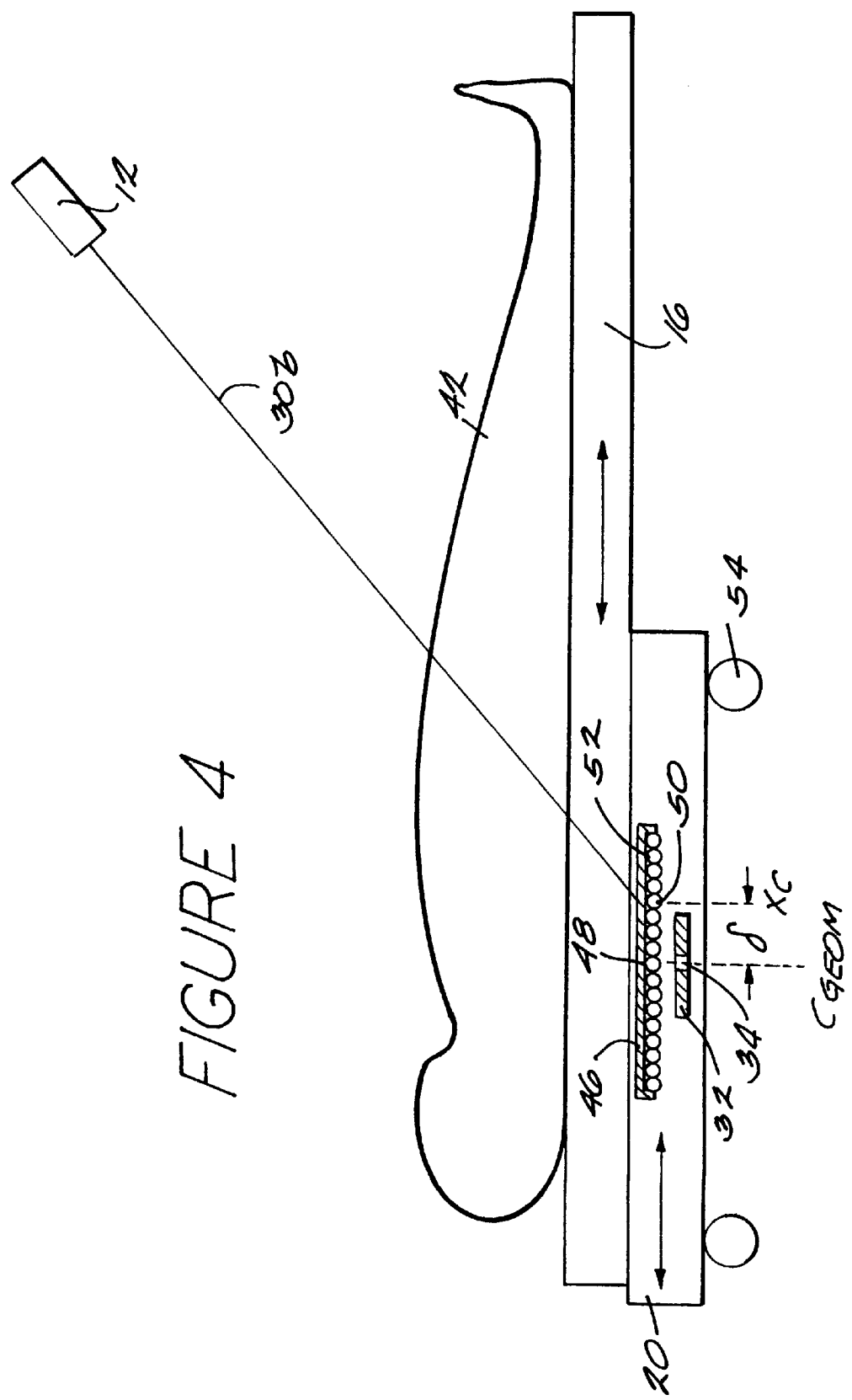
FIGS. 4–7 are schematic diagrams which respectively show components of the system of FIG. 1 in simplified form, together with respective useful embodiments of the invention.

Referring to FIG. 4, there is shown a linear LED array 46 mounted along the edge of detector 20. Array 46 comprises a center LED 48 and a number of other LED's 52 which extend to right and left of center LED 48, as viewed in FIG. 4, at regular intervals such as one-eighth inch. FIG. 4 further shows handle 32 of detector 20 fixably joined thereto so that mark 34 of the handle 32 is aligned with center LED 48. Thus, center LED 48 of array 46 is positioned at the center or midpoint of detector 20, with respect to the X-axis. Moreover, handle 34 and array 46 are joined to detector 20 for movement therewith, detector 20 being mounted for translational movement along the X-axis by means of rollers 54 or the like.

To use the arrangement of FIG. 4, an operator adjusts X-ray tube 12 and collimator 24 for a specified imaging procedure, whereby the respective parameters needed to compute offset $\delta$, as described above, are made available. After control device 36 has computed offset $\delta$, it sends a signal to array 46 to energize or illuminate an LED 50, which is spaced apart by the amount $\delta$ from center LED 48. The operator then translates the detector 20 to align the illuminated LED 50 with shadow line axis 30b of light field 28. LED 50 is thereby aligned along the X-axis with the point $X_c$ of light field 28, and also with the point $X_c$ of the X-ray beam FOV. Moreover, the illuminated LED 50 is positioned with respect to center LED 48 so that when the LED 50 is aligned at point $X_c$, center LED 48 and mark 34 will be aligned with the geometric center of the beam field. For example, if device 36 determines that offset $\delta$ is four-eighths inch and is located to the left of point $X_c$, the fourth LED to the right of center LED 48 would be energized. Thus, by simply aligning light field axis 30b with the energized LED 50, an operator may very expeditiously align the center of the detector with the geometric center of the X-ray FOV, along the X-axis.

While FIG. 4 shows a linear array 46 comprising light emitting diodes 52, within the scope of the invention other types of light emitting elements could be substituted therefor. As used herein, the term "light emitting element" refers to any type of small element, including but not limited to LED's, which can be placed in a linear array with other elements of like type, wherein each of the light emitting elements can be discretely or individually energized to produce a viewable light.

Figure 5:
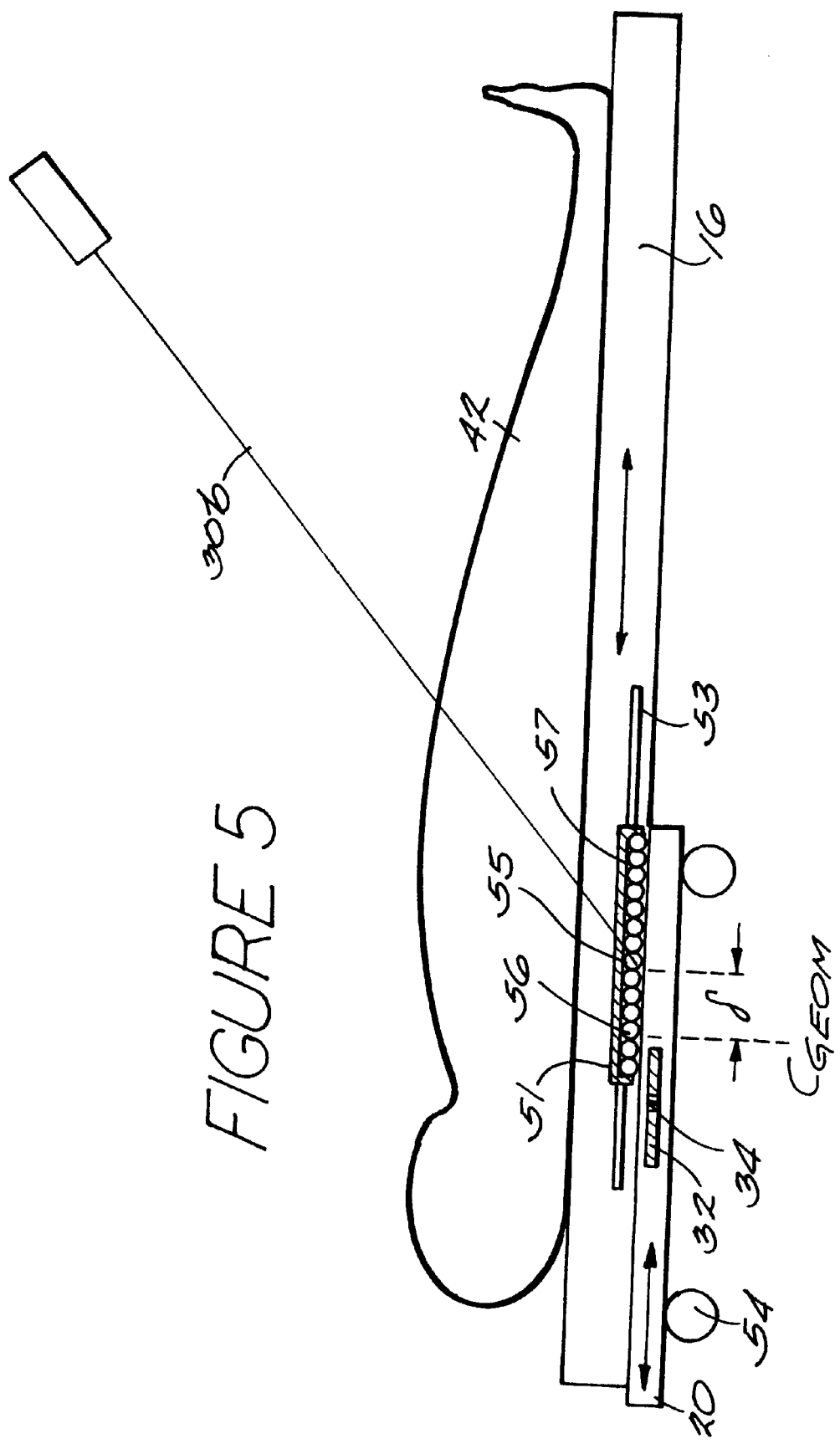

It will be apparent that the precision of alignment using an array of light emitting elements will be determined by the width of respective light emitting elements and the spacing therebetween. It is anticipated that control 36 will be able to select the correct element for illumination. Referring to FIG. 5, there is shown an LED array 51 mounted on the edge of table 16, for translational movement along the X-axis, by means of rails 53 or the like. Array 51 comprises a center LED 55, and a number of other LED's 57 which extend to right and left of center LED 55, as viewed in FIG. 5, at regular intervals such as one-eighth inch. Usefully, center LED 55 and the remaining LED's 57 are of different colors, such as amber and green, respectively. FIG. 5 further shows detector 20 mounted for translational movement along the X-axis by means of rollers 54 or the like.

To use the arrangement of FIG. 5, an operator adjusts X-ray tube 12 and collimator 24 for a specified imaging procedure, whereby the respective parameters needed to compute offset δ, as described above, are made available. The operator then translates LED array 51 to align center LED 55 with shadow line axis 30b of light field 28. LED 55 is thereby aligned along the X-axis with the point $X_c$ of light field 28, and also with the point $X_c$ of the X-ray beam FOV. After control device 36 has computed offset δ, it sends a signal to array 51 to energize the LED 56, which is spaced apart an amount δ from center LED 55. For example, if device 36 determines that offset δ is five-eighths inch and is located to the left of point $X_c$, the fifth LED to the left of center LED 55 would be energized. The operator would then align mark 34 on detector 20 with energized LED 56, to align the center of the detector with the geometric center of the X-ray FOV, along the X-axis.

Figure 6:
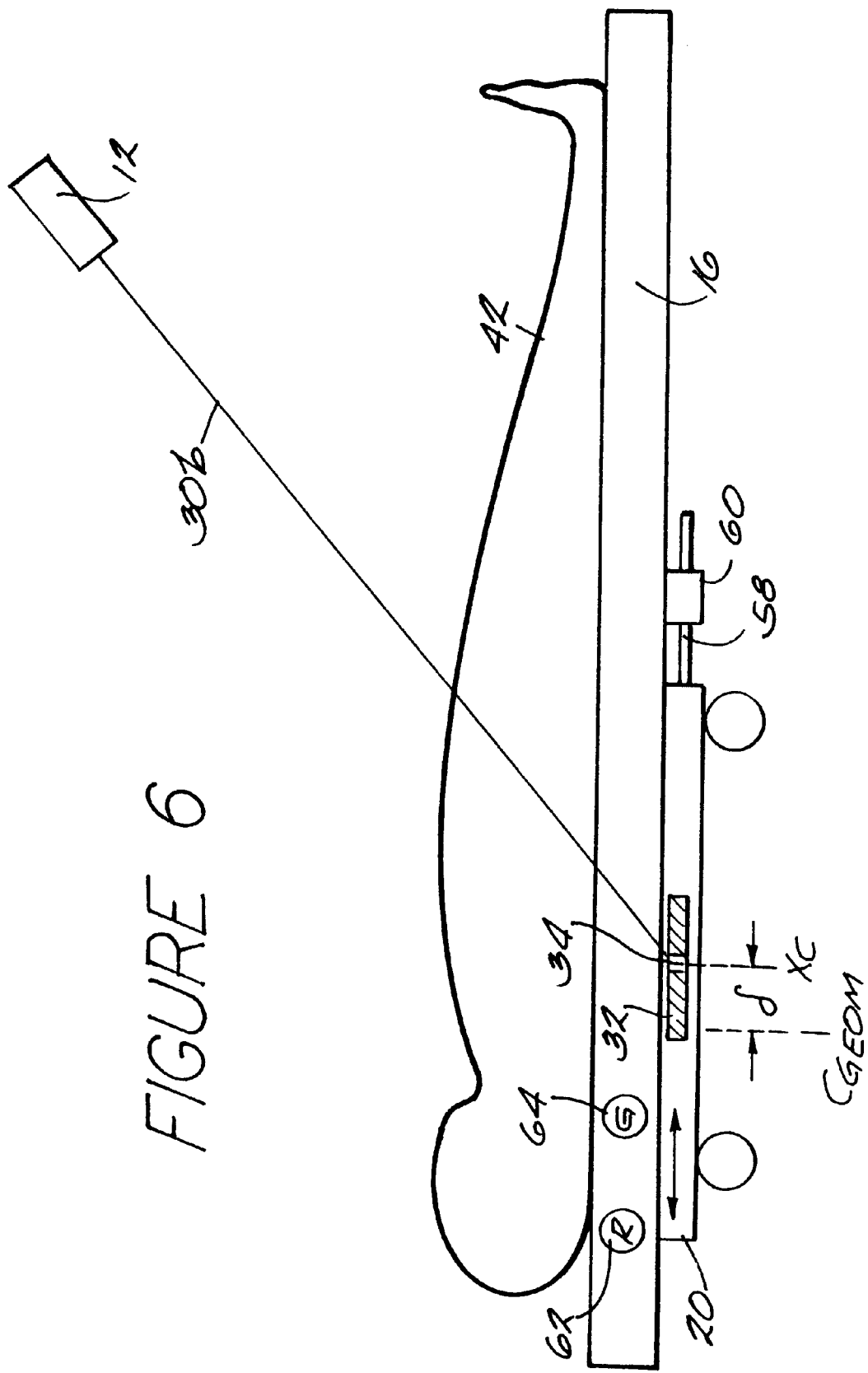

Referring to FIG. 6, there is again shown detector 20 mounted for translation along the X-axis by rollers 54 or the like. There is further shown a rod 58 fixably joined to an end of detector 20 for movement therewith, rod 58 being provided with markings or other indicia (not shown) at regular intervals along its length. As rod 58 translates with detector 20, it moves through a potentiometer, a magnetic detector or other device 60, of a type known in the art, which is disposed to register a count each time one of the rod markings passes a reference point in the device 60. Thus, device 60 provides a signal representing distance traveled by detector 20, and also indicates direction of travel. Referring further to FIG. 6, there is shown a red LED 62 and a green LED 64, both joined to table 16.

In operation, an operator aligns mark 34 on detector handle 32 with light field axis 30b. Thus, detector 20 is initially centered at the point $X_c$ of the X-ray FOV. After offset δ has been computed, the red LED 62 is energized if δ is non-zero. The operator randomly translates detector 20, and detector device 60 continually produces a signal representing displacement of detector 20. This signal is received by control device 26, which continually compares detector displacement with the computed offset δ. When device 26 determines that detector displacement is equal to offset δ, it energizes green LED 64, to inform the operator that the center of the detector 20 has been moved to the position of the geometric center of the X-ray beam FOV, along the X-axis.

Figure 7:
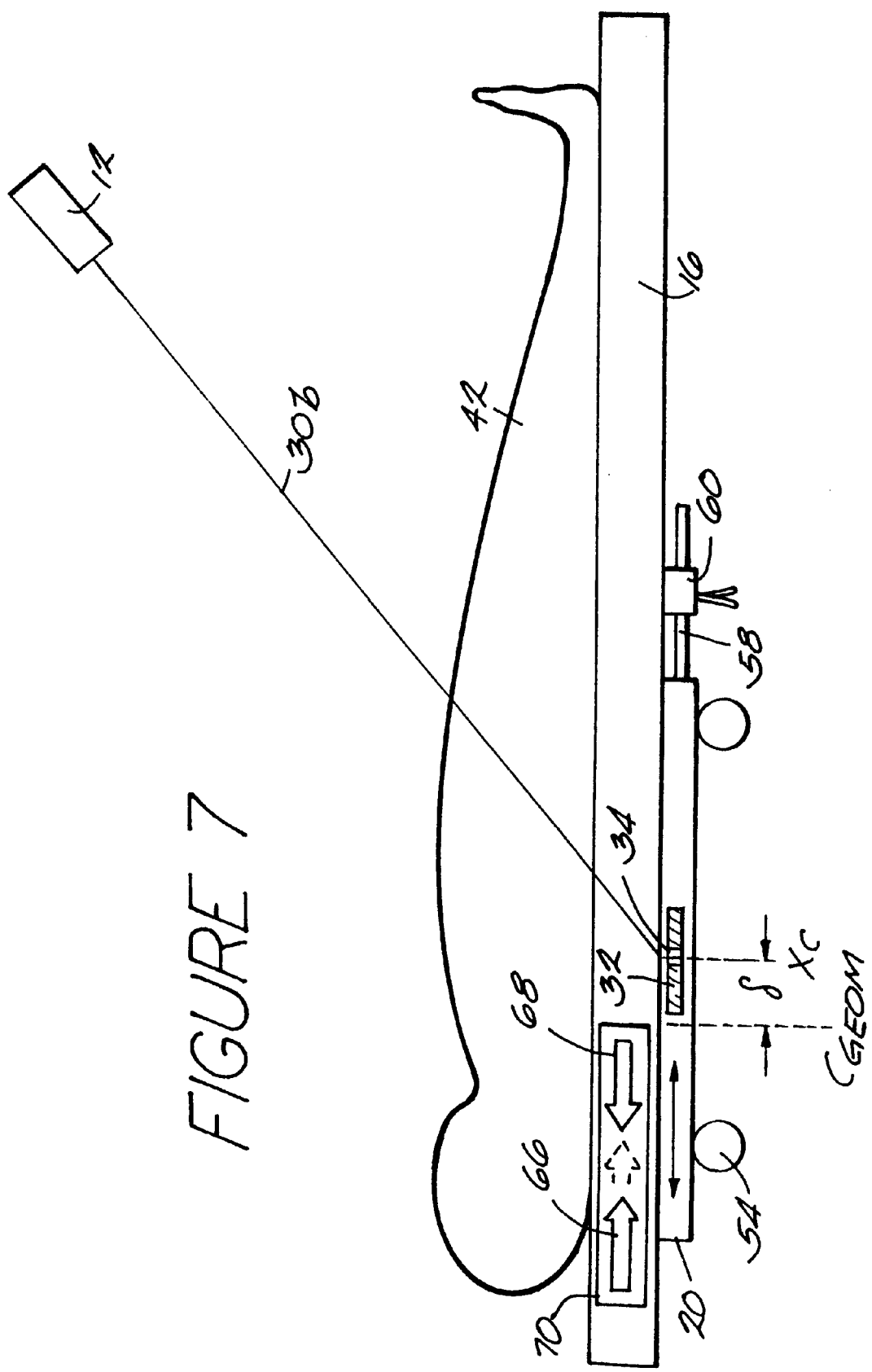

Referring to FIG. 7, there is shown an arrangement similar to the embodiment described above in connection with FIG. 5. However, a display device 70, mounted on table 16, has been substituted for the LED's 62 and 64. Display device 70 shows two arrows 66 and 68, which point in right and left direction, respectively, as viewed in FIG. 7. As with FIG. 6, mark 34 of the detector handle is initially aligned with axis 30b of the light field 28. After control device 26 computes offset δ, it operates display device 70 to show the tips of arrows 66 and 68 spaced apart by an amount equal to δ. Also, the arrow pointing in the direction which detector 20 must be moved appears brighter than the other arrow. When mark 34 of detector 20 is aligned with the geometric center of the beam field, the tips of arrows 66 and 68 are shown to be in contact.

Obviously, many other modifications and variations of the present invention are possible in light of the above teachings. It is therefore to be understood that within the scope of the disclosed concept, the invention may be practiced otherwise than as has been specifically described.

What is claimed is:

1. In an imaging system provided with a detector having a plane and an X-ray tube disposed to project an X-ray beam into the plane to define a beam field therein, apparatus comprising:

a viewable element fixably joined to said detector for indicating the position of said detector along a reference axis lying in said detector plane;

a device for computing the offset along said reference axis between the geometric center of said beam field and the point at which the central axis of said projected beam intersects said detector plane; and a viewable indicator device responsive to said offset for providing notice that said viewable element is positioned in prespecified relationship with said beam field geometric center.

2. In an imaging system provided with a detector having a plane and with an X-ray tube spaced apart from the plane, wherein the tube projects an X-ray beam into the plane and the projection defines a beam field therein, apparatus for use in selectively aligning said detector and said beam field comprising:

a first element indicating the position of said detector along a reference axis lying in said detector plane, said detector provided with an X-ray detection surface lying in said plane, said surface having a length dimension extending along said reference axis, and said first element comprising a visually observable element positioned at the center of said length dimension;

a computational device for producing a signal representing the offset along said reference axis between the geometric center of said beam field and the point at which the central axis of said projected beam intersects said detector plane;

structure respectively supporting said tube and said detector to enable relative translational motion therebetween along said reference axis; and an indicator device responsive to said produced signal for providing viewable notice when said first element and said beam field geometric center are aligned along said reference axis.

3. The apparatus of claim 2 wherein:

said computational device is disposed to compute said offset as a function of the spacing between said tube and said detector plane, and of angles respectively characterizing the direction and width of said projected beam.

4. The apparatus of claim 3 wherein:

said beam width angle is computed from said spacing, from said beam direction angle, and from a dimension of said beam field which extends along said reference axis.

5. The apparatus of claim 3 wherein:

said indicator device comprises a linear array of light emitting elements extending along said reference axis in parallel relationship, a given one of said light emitting elements being illuminated by said signal for use as a reference point in aligning said first element of said detector with said beam field geometric center; and said detector is supported for translational motion along said reference axis with respect to said light emitting element array to enable said first element and said given light emitting element to be brought into alignment.

6. The apparatus of claim 3 wherein said apparatus comprises:

a second element indicating the position of said central axis intersection point; and a tracking device disposed to monitor the linear travel of said detector along said reference axis, from an initial position at which said first and second elements are in alignment.

7. The apparatus of claim 6 wherein:

said indicator device comprises first and second light emitting elements of different colors, said first light emitting element being illuminated only when said first element is aligned with a location which is displaced along said reference axis, by a distance equal to said offset, from the location of said second element, and said second light emitting element is illuminated when said first element is not aligned with said location displaced from said second element location.

8. The apparatus of claim 6 wherein:

said indicator device comprises a display disposed to indicate the direction and distance required to translate said detector, along said reference axis, in order to align said first element with said beam field geometric center.

9. In an imaging system provided with a detector having a plane and an X-ray tube diposed to project an X-ray beam into the plane to define a beam field therein, apparatus comprising:

a first viewable reference means for identifying the position of the center point of said detector along a reference axis lying in said detector plane;

means for computing the offset along said reference axis between the geometric center of said beam field and the point at which the central axis of said projected beam intersects said detector plane; and a viewable indicator means responsive to said offset for indicating that said first viewable reference means is positioned in prespecified relationship with said beam field geometric center.

10. The apparatus of claim 9 wherein:

said computing means determines said offset as a function of the spacing between said tube and said detector plane, and of angles respectively characterizing the direction and width of said projected beam.

11. The apparatus of claim 10 wherein:

said computing means determines said beam width angle from said spacing, from said beam direction angle, and from a dimension of said beam field which extends along said reference axis.

12. The apparatus of claim 9 wherein:

said apparatus includes a second viewable reference means for identifying the position of said central axis intersection point.

13. The apparatus of claim 12 wherein:

said viewable indicator means comprises a linear array of LED's extending along said reference axis in spaced apart parallel relationship, a central LED being located at the midpoint of said array, and a given one of said LED's being illuminated by a signal representing said offset to indicate that said given LED is in alignment along said reference axis with said beam field geometric center;

said apparatus includes means for supporting said LED array for translational motion along said reference axis to align said central LED with said second viewable reference means; and said apparatus further includes means for supporting said detector for translational motion along said reference axis with respect to said LED array to align said first viewable reference means and said given LED.

14. The apparatus of claim 12 wherein:

said viewable indicator means comprises first and second LED's of different colors, said first LED being illuminated only when said first viewable reference means is spaced apart by said offset, along said reference axis, from the location of said second viewable reference means, and otherwise said second LED is illuminated; and said apparatus includes tracking means for monitoring the linear travel of said detector along said reference axis, from an initial position at which said first and second viewable reference means are in alignment.

15. The apparatus of claim 12 wherein:

said viewable indicator means comprises a visual display disposed to indicate the direction and distance required to translate said detector, along said reference axis, in order to align said first viewable reference means with said beam field geometric center; and said apparatus includes tracking means for monitoring the linear travel of said detector along said reference axis, from an initial position at which said first and second viewable reference means are in alignment.

16. In an imaging system provided with a detector having a plane and an X-ray tube disposed to project an X-ray beam into the plane to define a beam field therein, a method for selectively aligning said detector and said beam field comprising the steps of:

generating a signal representing the offset, along a reference axis lying in said plane, between the geometric center of said beam field and the point at which the central axis of said projected beam intersects said detector plane;

employing a viewable reference element to determine the position of said central axis intersection point; and coupling said signal to a viewable indicator device to operate said device to provide indication that a mark identifying the center point of said detector along said reference axis is positioned in prespecified relationship with said beam field geometric center.

17. The method of claim 16 wherein:

said signal generating step comprises computing said offset as a function of the spacing between said tube and said detector plane, and of angles respectively characterizing the direction and width of said projected beam.

18. The method of claim 17 wherein:

said viewable reference element comprises a viewable axis lying across a light field which substantially coincides with said X-ray beam field.

19. The method of claim 18 wherein:

a central LED in a linear LED array, which extends along said reference axis in spaced apart parallel relationship, is aligned with said viewable axis;

said signal is coupled to said array to illuminate a given one of said LED's; and said identifying mark of said detector is aligned with said given LED.

20. The method of claim 18 wherein:

said identifying mark of said detector is initially aligned with said viewable axis; and following said initial alignment, said signal operates a visual display to indicate the direction and distance required to translate said detector, along said reference axis, in order to align said identifying mark of said detector with said beam field geometric center.

* * * * *